(12) United States Patent
Ai

(10) Patent No.: US 11,439,681 B2
(45) Date of Patent: Sep. 13, 2022

(54) TRADITIONAL CHINESE MEDICINE COMPOSITION FOR TREATING TYPE 2 DIABETES

(71) Applicant: Jinchang Ai, Yueyang (CN)

(72) Inventor: Jinchang Ai, Yueyang (CN)

(*) Notice: Subject to any disclaimer, the term of this patent is extended or adjusted under 35 U.S.C. 154(b) by 136 days.

(21) Appl. No.: 17/120,207

(22) Filed: Dec. 13, 2020

(65) Prior Publication Data
US 2021/0330730 A1    Oct. 28, 2021

(30) Foreign Application Priority Data
Apr. 26, 2020  (CN) .......................... 202010339223.6

(51) Int. Cl.
| | | |
|---|---|---|
| *A61K 36/73* | (2006.01) | |
| *A61K 36/11* | (2006.01) | |
| *A61K 36/185* | (2006.01) | |
| *A61K 36/258* | (2006.01) | |
| *A61K 36/288* | (2006.01) | |
| *A61K 36/53* | (2006.01) | |
| *A61K 36/605* | (2006.01) | |
| *A61K 36/82* | (2006.01) | |
| *A61K 36/899* | (2006.01) | |

(52) U.S. Cl.
CPC .............. *A61K 36/73* (2013.01); *A61K 36/11* (2013.01); *A61K 36/185* (2013.01); *A61K 36/258* (2013.01); *A61K 36/288* (2013.01); *A61K 36/53* (2013.01); *A61K 36/605* (2013.01); *A61K 36/82* (2013.01); *A61K 36/899* (2013.01)

(58) Field of Classification Search
CPC ........ A61K 36/73; A61K 36/11; A61K 36/12; A61K 36/899; A61K 36/07; A61K 36/605; A61K 36/85; A61K 36/53; A61K 36/258; A61K 36/288; A61K 36/82; A61K 36/185
See application file for complete search history.

(56) References Cited

FOREIGN PATENT DOCUMENTS

KR    20210124511 A  * 10/2021  ............. A61K 45/06

* cited by examiner

*Primary Examiner* — Aaron J Kosar
(74) *Attorney, Agent, or Firm* — Harness, Dickey & Pierce, P.L.C.

(57) ABSTRACT

The application discloses a traditional Chinese medicine composition for treating of type 2 diabetes, comprising the following raw materials: wild Descolor Cinquefoil Herb, wild Rhizoma imperatae, wild Root and Rhizome of Japanese Climbing Fern, Ginseng leaf (over 7 years), wild Rough Melic, wild *Vitex negundo* L., *Morus alba* L., green tea, wild auricularia, corn silk, dandelion root. The traditional Chinese medicine composition of the application is suitable for patients with type 2 diabetes and complications of type 2 diabetes, which has no adverse reactions and stable curative effect.

20 Claims, No Drawings

TRADITIONAL CHINESE MEDICINE COMPOSITION FOR TREATING TYPE 2 DIABETES

CROSS REFERENCE TO RELATED APPLICATION

This application claims the priority of Chinese Patent Application No. 202010339223.6, entitled "Traditional Chinese medicine composition for treating type 2 diabetes" filed with China National Intellectual Property Administration on Apr. 26, 2020, which is incorporated herein by reference in its entirety.

FIELD

The disclosure relates to the field of traditional Chinese medicine, and in particular to a traditional Chinese medicine composition for treating type 2 diabetes.

BACKGROUND

Type 2 diabetes is the most common type of diabetes, which is also known as adult-onset diabetes because it mostly occurs in adults. The disease, caused by a variety of factors, can lead to insufficient insulin secretion in the body or the inability of the human body to effectively use insulin, resulting in a continuous increase in blood glucose level. In the hyperglycemic body environment, great vessels, microvessels, nerves, etc. will have diseases, which will harm the hearts, kidneys, eyes and other organs. Type 2 diabetes is a lifelong disease that cannot be fundamentally cured. However, long-term blood glucose control can prevent the occurrence of various complications, so that the disease can be relived for a long time and a good quality of life can be achieved. However, if the blood glucose cannot be controlled to the standard level for a long time. It is conceivable that various serious complications will occur. At present, there is no fundamental cure for type 2 diabetes in Western medicine, and also, the related symptoms are controlled by various drugs, with limited efficacy and many side effects.

Therefore, it is necessary to propose a traditional Chinese medicine composition for treating type 2 diabetes to solve the above-mentioned problems.

SUMMARY

In order to solve the above technical problems, the present disclosure provides a traditional Chinese medicine composition for treating type 2 diabetes. The traditional Chinese medicine composition is suitable for patients with type 2 diabetes. It has no adverse reactions and stable curative effect.

The present disclosure provides a traditional Chinese medicine composition for treating type 2 diabetes, consisting of the following raw materials: wild Descolor Cinquefoil Herb, wild Rhizoma imperatae, wild Root and Rhizome of Japanese Climbing Fern, Ginseng leaf (over 7 years), wild Rough Melic, wild *Vitex negundo* L., *Morus alba* L., green tea, wild auricularia, corn silk, dandelion root.

In some embodiments, the traditional Chinese medicine composition is made of the following weight ratio of raw materials: 15-25 g wild Descolor Cinquefoil Herb, 15-25 g wild Rhizoma imperatae, 15-25 g wild Root and Rhizome of Japanese Climbing Fern, 10-20 g Ginseng leaf (over 7 years), 10-20 g wild Rough Melic, 10-20 g wild *Vitex negundo* L., 10-20 g *Morus alba* L., 10-20 g green tea, 10-20 g wild auricularia, 10-20 g corn silk, 10-20 g dandelion root.

In one embodiment, the traditional Chinese medicine composition is made of the following weight ratio of raw materials: 15 g wild Descolor Cinquefoil Herb, 15 g wild Rhizoma imperatae, 15 g wild Root and Rhizome of Japanese Climbing Fern, 10 g Ginseng leaf (over 7 years), 10 g wild Rough Melic, 10 g wild *Vitex negundo* L., 10 g *Morus alba* L., 10 g green tea, 10 g wild auricularia, 10 g corn silk, 10 g dandelion root.

In another embodiment, the traditional Chinese medicine composition is made of the following weight ratio of raw materials: 25 g wild Descolor Cinquefoil Herb, 25 g wild Rhizoma imperatae, 25 g wild Root and Rhizome of Japanese Climbing Fern, 20 g Ginseng leaf (over 7 years), 20 g wild Rough Melic, 20 g wild *Vitex negundo* L., 20 g *Morus alba* L., 20 g green tea, 20 g wild auricularia, 20 g corn silk, 20 g dandelion root.

In yet another embodiment, the traditional Chinese medicine composition is made of the following weight ratio of raw materials: 20 g wild Descolor Cinquefoil Herb, 20 g wild Rhizoma imperatae, 20 g wild Root and Rhizome of Japanese Climbing Fern, 15 g Ginseng leaf (over 7 years), 15 g wild Rough Melic, 15 g wild *Vitex negundo* L., 15 g *Morus alba* L., 15 g green tea, 15 g wild auricularia, 15 g corn silk, 15 g dandelion root.

The traditional Chinese medicine composition can be made into decoctions, powders, pills or capsules and other dosage forms suitable for applying.

The beneficial effects of the embodiments: the traditional Chinese medicine composition of the embodiments may clear heat and promote fluid production, nourish liver and kidney, induce diuresis and detumescence. The traditional Chinese medicine composition is suitable for patients with type 2 diabetes. It has no adverse reactions and stable curative effect.

DETAILED DESCRIPTION

In order to make the above purpose, features and advantages of the present disclosure more obvious and understandable, the embodiments of the present disclosure are described specifically. In the following description, many specific details are explained in order to fully understand the present disclosure. However, the present disclosure can be implemented in many other ways different from those described embodiments, and one person skilled in the art can make similar improvements without violating the connotation of the present disclosure. Therefore, the present disclosure is not limited by the specific embodiments disclosed below.

The present disclosure will be further described below in combination with the examples.

Example 1

15 g wild Descolor Cinquefoil Herb, 15 g wild Rhizoma imperatae, 15 g wild Root and Rhizome of Japanese Climbing Fern, 10 g Ginseng leaf (over 7 years), 10 g wild Rough Melic, 10 g wild *Vitex negundo* L., 10 g *Morus alba* L., 10 g green tea, 10 g wild auricularia, 10 g corn silk, 10 g dandelion root were taken and prepared into the traditional Chinese medicine composition.

Example 2

25 g wild Descolor Cinquefoil Herb, 25 g wild Rhizoma imperatae, 25 g wild Root and Rhizome of Japanese Climbing Fern, 20 g Ginseng leaf (over 7 years), 20 g wild Rough Melic, 20 g wild *Vitex negundo* L., 20 g *Morus alba* L., 20 g green tea, 20 g wild auricularia, 20 g corn silk, 20 g dandelion root were taken and prepared into the traditional Chinese medicine composition.

Example 3

20 g wild Descolor Cinquefoil Herb, 20 g wild Rhizoma imperatae, 20 g wild Root and Rhizome of Japanese Climbing Fern, 15 g Ginseng leaf (over 7 years), 15 g wild Rough Melic, 15 g wild *Vitex negundo* L., 15 g *Morus alba* L., 15 g green tea, 15 g wild auricularia, 15 g corn silk, 15 g dandelion root were taken and prepared into the traditional Chinese medicine composition.

The traditional Chinese medicine composition of the present disclosure can be made into various dosage forms suitable for application such as decoctions, powders, pills or capsules, and can also be added to drinks.

As for the characteristics of said components of the traditional Chinese medicine composition of the present disclosure, wherein:

Wild Descolor Cinquefoil Herb: characterized by sweet, slight bitter, mild in nature, and with the efficacy of clearing heat and removing toxicity, cooling blood for hemostasis, curing dysentery, curing leukorrhea, inducing detumescence and lowering blood glucose.

Wild Rhizoma imperatae: characterized by cold in nature, sweet in taste, and with the efficacy of promoting fluid production, quenching thirst, reducing fever and causing diuresis, hemostasis and protecting liver, and effectively preventing cardiovascular and cerebrovascular diseases.

Wild Root and Rhizome of Japanese Climbing Fern: characterized by sweet, light in taste, cold in nature, and with the efficacy of clearing heat and removing toxicity, removing dampness and reducing swelling. It can be used for treating pneumonia, cold and high fever, Japanese encephalitis, acute gastroenteritis, dysentery, infectious acute icteric hepatitis, urinary tract infection and other diseases.

Ginseng leaf (over 7 years): characterized by bitter, sweet in taste, cold in nature; classified into meridian tropism of lung and stomach, and with the efficacy of tonifying Qi, benefiting lung, driving away summer heat and promoting fluid production. It can be used for treating Qi-asthenia cough, being agitated due to summer heat, thirst caused by secretion injury, head and eyes being unclear and limbs fatigue.

Wild Rough Melic: characterized by cool in nature, sweet in taste, and with the efficacy of cooling and clearing heat, removing toxicity, inducing diuresis and relieving stranguria. It can be used for treating diabetes, jaundice hepatitis and other diseases.

Wild *Vitex negundo* L.: characterized by pungent, bitter in taste, mild in nature, and with the efficacy of relieving exterior syndrome by expelling wind, relieving cough and asthma, regulating Qi, promoting digestion and relieving pain. It can be used for cold, cough, asthma, stomachache and acid regurgitation, dyspepsia, dysentery due to food accumulation, cholecystitis, cholelithiasis and hernia.

*Morus alba* L.: It has the efficacy of coursing wind and dissipating heat, clearing lung and moisturizing dryness, clearing liver and brightening the eyes. It has the functions of preventing and treating wind-heat type common cold, lung heat and dry-cough, swollen sore throat, hematasthenic headache, eye fatigue, habitual constipation, dysuria and rheumatic arthralgia. It also has the functions of lowering blood pressure and blood glucose, reducing blood lipid, preventing cerebral thrombosis, losing weight and health care. Modern researches have confirmed that the extract of mulberry leaf can not only lower blood glucose, but also relieve some complications of diabetes, such as retinopathy.

Wild auricularia: characterized by mild in nature, sweet, light in taste, non-toxic, with the efficacy of moistening lung and promoting fluid production, nourishing Yin and stomach, replenishing Qi for tranquilization, powering up heart and brain.

Green tea: It has the efficacy of bringing up the spirit and clearing the heart, clearing and removing heat, promoting digestion and dissipating phlegm, removing greasiness and weight reduction, clearing the heart and relieving restlessness, removing toxicity and sobering, promoting fluid production and quenching thirst, elimating pathogenic fire and brightening the eyes, curing dysentery and removing dampness. It has certain pharmacological efficacy on modern diseases, such as radiation sickness, cardio-cerebrovascular disease, cancer and other diseases.

Corn silk: characterized by sweet, light in taste, mild in nature, with the efficacy of inducing diuresis and detumescence, clearing liver and improving choleresis. It is mainly used for edema, dribble of urine, jaundice, cholecystitis, cholelithiasis, hypertension, diabetes, and milk blocking.

Dandelion root: characterized by sweet, slight bitter in taste, with the efficacy of clearing heat and removing toxicity, inducing diuresis, relieving diarrhea, treating jaundice and improving choleresis.

In the composition of the present disclosure, wild Descolor Cinquefoil Herb, wild Rhizoma imperatae, wild Root and Rhizome of Japanese Climbing Fern are the sovereign drugs, which have the efficacy of clearing heat and promoting fluid production, removing dampness and reducing swelling; Ginseng leaf (over 7 years), wild Rough Melic and wild *Vitex negundo* L., which are minister drugs, have the efficacy of replenishing Qi and reinforcing deficiency, clearing heat and promoting fluid production; *Morus alba* L., green tea, wild auricularia, corn silk and dandelion root, which are the assistant drug, have the efficacy of nourishing liver and brightening the eyes, clearing heat and promoting fluid production, inducing diuresis and detumescence. The prescription have the efficacy of clearing heat and promoting fluid production, nourishing liver and kidney, and inducing diuresis and detumescence.

The traditional Chinese medicine composition of present disclosure has the advantages of scientific and rational composition, safe compatibility and medication. In order to prove the therapeutic effect of the traditional Chinese medicine composition, clinical observation data of 100 relevant patients was provided and screened. These 100 cases were randomly divided into two groups, i.e. 52 cases in the treatment group and 48 cases in the control group. There was no statistically significant difference between the two groups of patients in terms of their condition and basic individual information. The two groups were comparable.

1. Selection Criteria:

Patients with type 2 diabetes and complications of type 2 diabetes can be used as criteria for selecting cases.

2. Diagnostic Criteria:

Polydipsia, polyuria, polyphagia and emaciation; fatigue weakness, obesity; blurred vision, edema and oliguria.

3. Implementation Plan:

Treatment group: the traditional Chinese medicine composition of the present disclosure was made into decoction, which was taken in the morning and evening, 300-500 ml each time, One month is a course of treatment, and it was counted after a course of treatment.

Control group: Xiaoke pills (diabetes pills) were taken orally in accordance with the drug regulations, One month is a course of treatment, and it was counted after a course of treatment.

4. Control Results

In the treatment group, 30 cases(57.7%) were improved. 15 cases (28.8%) were effective. 7 cases (13.5%) were ineffective and the total effective rate was 86.5%. In the control group, the condition of 17 (35.4%) cases was improved, 12 cases (25%) were effective. 19 cases (39%) were ineffective and the total effective rate was 60.4%; wherein, the 'improved' refers to symptom reduction according to the patients' self-feeling, or diagnosis results by medical devices and traditional Chinese medicine, the 'effective' refer to the patients' condition that is under control, while the 'ineffective' refers to ineffective symptoms and no obvious improvement.

It can be seen from the observation results that the traditional Chinese medicine composition has a good therapeutic effect for patients with type 2 diabetes and complications of type 2 diabetes.

The traditional Chinese medicine composition of the present disclosure has been made into other formulation, and the same or similar results have been obtained in the other examples. In order to prevent cumbersomeness, the present disclosure will not list them all. Moreover, the disclosure claims to protect a traditional Chinese medicine composition (combined invention), not formulation or preparation method. Therefore, any formulation made of the traditional Chinese medicine composition of the present disclosure and used for the treatment of similar diseases belongs to the protection scope of the present disclosure.

What is claimed is:

1. A pharmaceutical composition for treating type 2 diabetes, comprising therapeutically effective amounts of the following raw materials: wild Descolor Cinquefoil Herb, wild Rhizoma imperatae, wild Root and Rhizome of Japanese Climbing Fern, Ginseng leaf of over 7 years, wild Rough Melic, wild *Vitex negundo* L., *Morus alba* L., green tea, wild Auricularia, corn silk, and dandelion root.

2. The pharmaceutical composition for treating type 2 diabetes according to claim 1, comprising the following weight ratio of said raw materials: 15-25 g wild Descolor Cinquefoil Herb, 15-25 g wild Rhizoma imperatae, 15-25 g wild Root and Rhizome of Japanese Climbing Fern, 10-20 g Ginseng leaf, 10-20 g wild Rough Melic, 10-20 g wild *Vitex negundo* L., 10-20 g *Morus alba* L., 10-20 g green tea, 10-20 g wild Auricularia, 10-20 g corn silk, and 10-20 g dandelion root.

3. The pharmaceutical composition for treating type 2 diabetes according to claim 2, comprising the following weight ratio of said raw materials: 15 g wild Descolor Cinquefoil Herb, 15 g wild Rhizoma imperatae, 15 g wild Root and Rhizome of Japanese Climbing Fern, 10 g Ginseng leaf, 10 g wild Rough Melic, 10 g wild *Vitex negundo* L., 10 g *Morus alba* L., 10 g green tea, 10 g wild Auricularia, 10 g corn silk, and 10 g dandelion root.

4. The pharmaceutical composition for treating type 2 diabetes according to claim 2, comprising the following weight ratio of said raw materials: 25 g wild Descolor Cinquefoil Herb, 25 g wild Rhizoma imperatae, 25 g wild Root and Rhizome of Japanese Climbing Fern, 20 g Ginseng leaf, 20 g wild Rough Melic, 20 g wild *Vitex negundo* L., 20 g *Morus alba* L., 20 g green tea, 20 g wild Auricularia, 20 g corn silk, and 20 g dandelion root.

5. The pharmaceutical composition for treating type 2 diabetes according to claim 2, comprising the following weight ratio of said raw materials: 20 g wild Descolor Cinquefoil Herb, 20 g wild Rhizoma imperatae, 20 g wild Root and Rhizome of Japanese Climbing Fern, 15 g Ginseng leaf, 15 g wild Rough Melic, 15 g wild *Vitex negundo* L., 15 g *Morus alba* L., 15 g green tea, 15 g wild Auricularia, 15 g corn silk, and 15 g dandelion root.

6. The pharmaceutical composition for treating type 2 diabetes according to claim 1, wherein traditional Chinese medicine composition is in the form of a decoction, powder, pill, or capsule.

7. The pharmaceutical composition for treating type 2 diabetes according to claim 6, comprising the following weight ratio of said raw materials: 15-25 g wild Descolor Cinquefoil Herb, 15-25 g wild Rhizoma imperatae, 15-25 g wild Root and Rhizome of Japanese Climbing Fern, 10-20 g Ginseng leaf, 10-20 g wild Rough Melic, 10-20 g wild *Vitex negundo* L., 10-20 g *Morus alba* L., 10-20 g green tea, 10-20 g wild Auricularia, 10-20 g corn silk, and 10-20 g dandelion root.

8. The pharmaceutical composition for treating type 2 diabetes according to claim 6, comprising the following weight ratio of raw materials: 15 g wild Descolor Cinquefoil Herb, 15 g wild Rhizoma imperatae, 15 g wild Root and Rhizome of Japanese Climbing Fern, 10 g Ginseng leaf, 10 g wild Rough Melic, 10 g wild *Vitex negundo* L., 10 g *Morus alba* L., 10 g green tea, 10 g wild Auricularia, 10 g corn silk, and 10 g dandelion root.

9. The pharmaceutical composition for treating type 2 diabetes according to claim 6, comprising the following weight ratio of raw materials: 25 g wild Descolor Cinquefoil Herb, 25 g wild Rhizoma imperatae, 25 g wild Root and Rhizome of Japanese Climbing Fern, 20 g Ginseng leaf, 20 g wild Rough Melic, 20 g wild *Vitex negundo* L., 20 g *Morus alba* L., 20 g green tea, 20 g wild Auricularia, 20 g corn silk, and 20 g dandelion root.

10. The pharmaceutical composition for treating type 2 diabetes according to claim 6, comprising the following weight ratio of raw materials: 20 g wild Descolor Cinquefoil Herb, 20 g wild Rhizoma imperatae, 20 g wild Root and Rhizome of Japanese Climbing Fern, 15 g Ginseng leaf, 15 g wild Rough Melic, 15 g wild *Vitex negundo* L., 15 g *Morus alba* L., 15 g green tea, 15 g wild Auricularia, 15 g corn silk, and 15 g dandelion root.

11. A method for treating type 2 diabetes in a subject, comprising administering the composition of claim 1 to said subject in need of such treatment.

12. A method for treating type 2 diabetes in a subject, comprising administering the composition of claim 2 to said subject in need of such treatment.

13. A method for treating type 2 diabetes in a subject, comprising administering the composition of claim 3 to said subject in need of such treatment.

14. A method for treating type 2 diabetes in a subject, comprising administering the composition of claim 4 to said subject in need of such treatment.

15. A method for treating type 2 diabetes in a subject, comprising administering the composition of claim 5 to said subject in need of such treatment.

16. A method for treating type 2 diabetes in a subject, comprising administering the composition of claim 6 to said subject in need of such treatment.

17. A method for treating type 2 diabetes in a subject, comprising administering the composition of claim 7 to said subject in need of such treatment.

18. A method for treating type 2 diabetes in a subject, comprising administering the composition of claim 8 to said subject in need of such treatment.

19. A method for treating type 2 diabetes in a subject, comprising administering the composition of claim 9 to said subject in need of such treatment.

20. A method for treating type 2 diabetes in a subject, comprising administering the composition of claim 10 to said subject in need of such treatment.

\* \* \* \* \*